(12) United States Patent
Badur et al.

(10) Patent No.: US 12,391,015 B2
(45) Date of Patent: Aug. 19, 2025

(54) PRODUCTION DEVICE AND PROCESS FOR PRODUCING AN INTRAOCULAR LENS BLANK, INTRAOCULAR LENS BLANK

(71) Applicant: CARL ZEISS MEDITEC AG, Jena (DE)

(72) Inventors: Thorben Badur, Oberkochen (DE); Stephen Q. Zhou, Oberkochen (DE); Minh Cao, Oberkochen (DE); Christoph Zumbach, Oberkochen (DE); Vincent Sunio, Oberkochen (DE); Alex Pfotenhauer, Oberkochen (DE); Karen Hong, Oberkochen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 18/834,285

(22) PCT Filed: Feb. 1, 2022

(86) PCT No.: PCT/US2022/014746
§ 371 (c)(1),
(2) Date: Jul. 30, 2024

(87) PCT Pub. No.: WO2023/149862
PCT Pub. Date: Aug. 10, 2023

(65) Prior Publication Data
US 2025/0107885 A1     Apr. 3, 2025

(51) Int. Cl.
*B29D 11/00*     (2006.01)
*A61F 2/16*      (2006.01)
*B29D 11/02*     (2006.01)

(52) U.S. Cl.
CPC .............. *B29D 11/023* (2013.01); *A61F 2/16* (2013.01); *A61F 2240/004* (2013.01)

(58) Field of Classification Search
CPC .......... B29D 11/02; B29D 11/023; A61F 2/16
See application file for complete search history.

(56) References Cited

U.S. PATENT DOCUMENTS

| | | |
|---|---|---|
| 5,137,441 A | 8/1992 | Fogarty |
| 5,620,720 A | 4/1997 | Glick et al. |
| 2020/0008931 A1 | 1/2020 | Argento et al. |

FOREIGN PATENT DOCUMENTS

| | | | |
|---|---|---|---|
| FR | 2841767 | * | 1/2004 |
| WO | WO 2014/038940 A1 | | 3/2014 |

OTHER PUBLICATIONS

International Search Report for International Application No. PCT/US2022/014746, mailed Apr. 18, 2022, (4 pages).

(Continued)

*Primary Examiner* — Mathieu D Vargot
(74) *Attorney, Agent, or Firm* — ALSTON & BIRD LLP

(57) ABSTRACT

Provided is a production device for producing an intraocular lens blank, with a first mold half, which has an outer ring, and a second mold half, which have a spacing state, in which the second mold half is arranged outside the outer ring, and a proximity state, in which the second mold half is clamped in the outer ring as a result of inserting the second mold half in an inserting direction, wherein the first mold half has a central region of the first mold half and the second mold half has a central region of the second mold half, wherein the second mold half has a bellows, which extends fully circumferentially around the central region of the second mold half in a circumferential direction with respect to an optical axis of the optical body and has a first bellows portion and a second bellows portion, which is arranged directly outside the first bellows portion in a radial direction with respect to the optical axis and, in the spacing state, forms with the first bellows portion a first angle ($\alpha$), which is smaller than 180°, (Continued)

Figure 1:
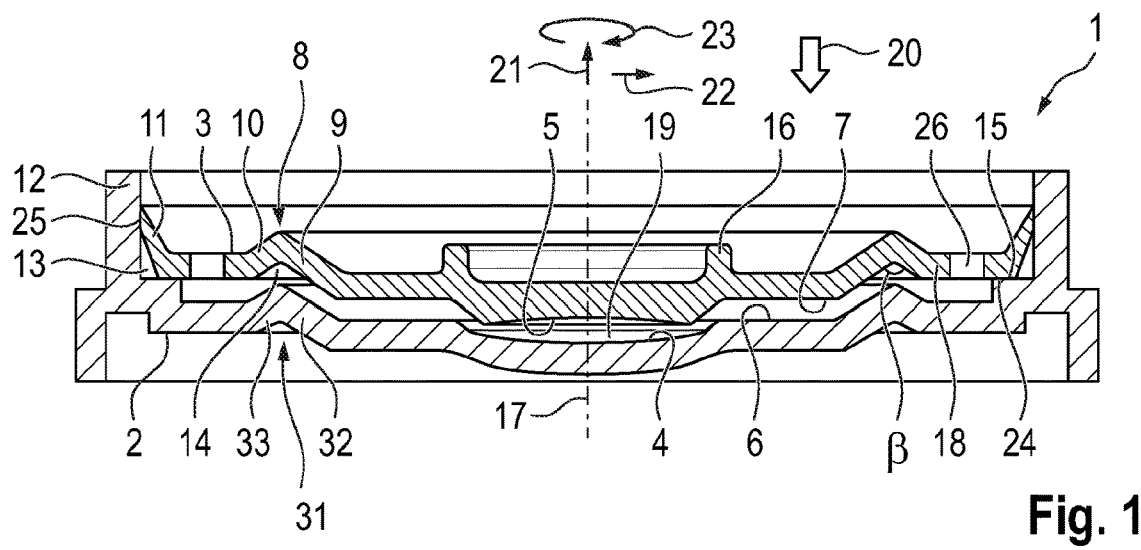

and, in the proximity state, forms with the first bellows portion a second angle ($\beta$), which is smaller than the first angle.

5 Claims, 3 Drawing Sheets

(56) References Cited

OTHER PUBLICATIONS

Written Opinion of the International Searching Authority (ISA/US) for International Application No. PCT/US2022/014746, mailed Apr. 18, 2022, (9 pages).

\* cited by examiner

PRODUCTION DEVICE AND PROCESS FOR PRODUCING AN INTRAOCULAR LENS BLANK, INTRAOCULAR LENS BLANK

CROSS-REFERENCE TO RELATED APPLICATIONS

The present application is a national phase entry of International Application No. PCT/US2022/014746, filed Feb. 1, 2022, which is incorporated herein by reference in its entirety.

The invention relates to a production device for producing an intraocular lens blank and to a process for producing the intraocular lens blank.

An intraocular lens is intended to replace a natural lens of a human in cataract treatment. The intraocular lens has an optical body, which is designed to carry out optical imaging, and a haptic element, which is intended to keep the optical body as close as possible to the middle of the eye in a capsular bag in which the natural lens was arranged before the cataract treatment. The optical body must in this case be produced with very low tolerances in order to avoid aberrations of the optical imaging. Conventionally, the intraocular lens may be produced for example by a molding process, in which a liquid is cured in a mold. This entails the problem that the liquid shrinks when it cures, which can lead to aberrations. It is also problematic that mechanical stresses can occur in the mold as a result of two parts of the mold being joined together. The mechanical stresses may lead to deformation of the mold, the deformation of the mold likewise potentially leading to the aberrations of the optical body.

The object of the invention is therefore to provide a production device for producing an intraocular lens blank, a process for producing the intraocular lens blank and an intraocular lens blank with which aberrations of an optical body of the intraocular lens blank can be avoided.

A first production device according to the invention for producing an intraocular lens blank has a first mold half, which has an outer ring, and a second mold half. The first mold half and the second mold half have a spacing state, in which the second mold half is arranged outside the outer ring, and a proximity state, in which the second mold half is clamped in the outer ring as a result of inserting the second mold half in an inserting direction, and the first mold half and the second mold half delimit a molding space in which a curable liquid is intended to be arranged for producing the intraocular lens blank. The first mold half has a central region of the first mold half and the second mold half has a central region of the second mold half, the central region of the first mold half and the central region of the second mold half respectively having the form of one of the two end faces of an optical body of the intraocular lens blank. The end faces are those faces of the optical body at which light passing through the lens is refracted in order to carry out optical imaging. The second mold half has a bellows, which extends fully circumferentially around the central region of the second mold half in a circumferential direction with respect to an optical axis of the optical body and has a first bellows portion and a second bellows portion, which is arranged directly outside the first bellows portion in a radial direction with respect to the optical axis and, in the spacing state, forms with the first bellows portion a first angle, which is smaller than 180°, and, in the proximity state, forms with the first bellows portion a second angle, which is smaller than the first angle.

A second production device for producing an intraocular lens blank, has a first mold half, which has an outer ring, and a second mold half, which have a spacing state, in which the second mold half is arranged outside the outer ring, and a proximity state, in which the second mold half is clamped in the outer ring as a result of inserting the second mold half in an inserting direction, and the first mold half and the second mold half delimit a molding space in which a curable liquid is intended to be arranged for producing the intraocular lens blank, wherein the first mold half has a central region of the first mold half and the second mold half has a central region of the second mold half, the central region of the first mold half and the central region of the second mold half respectively having the form of one of the two end faces of an optical body of the intraocular lens blank, wherein the end faces are those faces of the optical body at which light passing through the lens is refracted in order to carry out optical imaging, and the first mold half has a bellows, which extends fully circumferentially around the central region of the first mold half in a circumferential direction with respect to an optical axis of the optical body and has a first bellows portion and a second bellows portion, which is arranged directly outside the first bellows portion in a radial direction with respect to the optical axis and, in the spacing state, forms with the first bellows portion a first angle, which is smaller than 180°, and, in the proximity state, forms with the first bellows portion a second angle, which is larger than the first angle and in particular smaller than 180°.

According to the first production device, with the second mold half clamped in the outer ring of the first mold half, a mechanical stress is produced in the second mold half, originating from the end of the second mold half lying on the outside in the radial direction. This mechanical stress leads to deformation of the bellows in such a way that the first bellows portion and the second bellows portion come into closer proximity to one another, whereby the second angle becomes smaller than the first angle. Because the central region of the second mold half is arranged inside the bellows in the radial direction, the mechanical stresses cannot spread out, or only to a slight extent, to the central region of the second mold half. As a result, the central region of the second mold half is not deformed, or only slightly, whereby aberrations of the optical body can be avoided. The second production device works analogously.

It is preferred that, in the proximity state, the second mold half contacts the outer ring fully circumferentially in the circumferential direction, whereby a first seal is formed by the outer ring and the second mold half, fully circumferentially in the circumferential direction. As a result, contact of the liquid with oxygen, and consequently a reaction of the oxygen with the liquid, can be reduced. Moreover, as a result of the fully circumferential contact, the mechanical stresses are introduced uniformly into the second mold half and at the same time the proximity state is fixed particularly well.

The first mold half preferably has a stop, which extends fully circumferentially in the circumferential direction, the second mold half being designed to come up against the stop at the end of the insertion, whereby, in the proximity state, a second seal is formed by the stop and the second mold half, fully circumferentially in the circumferential direction. As a result, contact of the liquid with the oxygen can be reduced still further.

The second mold half preferably has a lip, which is that part of the second mold half that contacts the outer ring and projects from the rest of the second mold half counter to the inserting direction and outward in the radial direction, whereby, in the proximity state, an outer cavity is delimited by the lip and the outer ring. If the first mold half and the second mold half are brought into the proximity state, some of the liquid that is superfluous can get into the outer cavity. In the outer cavity, the liquid can act as a sacrificial liquid, in that it reacts with the oxygen and consequently uses up the oxygen before the oxygen can get any further inward in the radial direction. It is particularly preferred that the first seal and the second seal delimit the outer cavity.

It is preferred that, in the first production device in the proximity state, the first bellows portion forms the inner end of the bellows in the radial direction, and is thus inclined in relation to the optical axis such that a distance of the first bellows portion from the optical axis becomes shorter in the inserting direction, the central region of the second mold half being fastened to the inner end of the first bellows portion in the radial direction. This achieves the effect that, when deforming of the bellows occurs in the proximity state, caused by the first bellows portion coming into closer proximity to the second bellows portion, a displacement of the central region of the second mold half toward the first mold half may take place in an axial direction with respect to the optical axis. As a result, shrinking of the liquid due to its curing can be advantageously compensated. The length of the displacement can be made to match the magnitude of the change in volume of the optical body during the curing of the liquid. For determining the length of the displacement, for example FEM calculations and/or trials may be carried out, in which for example the magnitude of the first angle, the orientation of the second bellows portion, the thickness of the first bellows portion, the extent of the first bellows portion in the axial direction, the thickness of the second bellows portion and/or the extent of the second bellows portion in the radial direction are varied and, for each variation, the length of the displacement is respectively determined. The central region of the second mold half may be fastened directly to the first bellows portion of the central region of the second mold half may be fastened indirectly to the first bellows portion via a further region.

It is preferred that, in the second production device in the proximity state, the first bellows portion forms the inner end of the bellows in the radial direction, and is thus inclined in relation to the optical axis such that a distance of the first bellows portion from the optical axis becomes shorter against the inserting direction, the central region of the second mold half being fastened to the inner end of the first bellows portion in the radial direction.

It is conceivable that the first mold half and/or the second mold half have a further stop, by means of which a minimal thickness of the optical body can be established. As a result, the displacement in the event of shrinking of the liquid can be limited. The further stop may for example be arranged outside the central region of the first mold half and/or outside the central region of the second mold half in the radial direction.

For the first production device, in the proximity state, the second bellows portion is preferably oriented in the radial direction. Alternatively, it is preferred that, in the proximity state, the second bellows portion is inclined in relation to the optical axis such that a distance of the second bellows portion from the optical axis becomes longer in the inserting direction. For the second production device, in the proximity state, the second bellows portion is preferably oriented in the radial direction. Alternatively, it is preferred that, in the proximity state, the second bellows portion is inclined in relation to the optical axis such that a distance of the second bellows portion from the optical axis becomes longer against the inserting direction.

The first mold half preferably delimits an inner cavity, which is part of the molding space, is arranged outside the central region of the second mold half in the radial direction and, in the case where the inserting direction is oriented downward, is arranged above a region of the molding space, it being intended for the optical body to be formed in the region. In the case where the inserting direction is oriented downward, air bubbles trapped in the molding space possibly flow automatically into the inner cavity. There, the air bubbles cannot impair the forming of the optical body. The inner cavity may for example be delimited by the bellows, in particular by the first bellows portion and the second bellows portion.

The second mold half preferably has a haptic region of the second mold half, which is arranged in a radial region in which a haptic element is intended to be formed from the cured liquid in order to form an intraocular lens from the intraocular lens blank and which is arranged inside the bellows in the radial direction. Cured liquid from a radial region in which the bellows is arranged can be separated from the remaining cured liquid. The further region via which the central region of the second mold half can be fastened indirectly to the first bellows portion may have the haptic region of the second mold half or consist of the haptic region of the second mold half.

The second mold half preferably has a reinforcing projection, which projects counter to the inserting direction from regions of the second mold half adjacent to the reinforcing projection and is arranged inside the bellows in the radial direction. The provision of the reinforcing projection has the effect that the central region of the second mold half has less of a tendency to deform. The reinforcing projection is preferably annular and, in the proximity state, is arranged around the optical axis and in particular is arranged concentrically in relation to the optical axis. It is alternatively preferred that the reinforcing projection is cylindrical and, in the proximity state, is arranged concentrically in relation to the optical axis. The production device may have an assembly tool, which is designed to grip the reinforcing projection and to insert the second mold half in the inserting direction into the outer ring and/or remove it from the outer ring.

The first mold half preferably has a first marking, which is designed to mark a circumferential position of the first mold half, and the second mold half preferably has a second marking, which is designed to mark a circumferential position of the second mold half. As a result, a relative orientation of the first mold half in relation to the second mold half can be set, for example in that the second mold half is turned about the optical axis until the first marking and the second marking are oriented in the same radial direction. This may be relevant if the optical body is toric and in particular if the two end faces are not formed rotationally symmetrically. This also makes it possible to set the orientation of the optical body in relation to the first mold half or in relation to the second mold half during the process for producing the intraocular lens blank. It is also possible by turning the first mold half and/or the second mold half to set the orientation of the intraocular lens blank with respect to other devices involved in the process for producing the intraocular lens blank.

For the first production device, it is preferred that the first mold half has a further bellows, which extends fully circumferentially around the central region of the first mold half in a circumferential direction with respect to the optical axis and has a further first bellows portion and a further second bellows portion, which is arranged directly outside the further first bellows portion in a radial direction with respect to the optical axis and, in the spacing state, forms with the further first bellows portion a further first angle, which is smaller than 180°, and, in the proximity state, forms with the further first bellows portion a further second angle, which is smaller than the further first angle. As a result, mechanical stresses which occur in the proximity state and in the first mold half pass from the outer ring to the inside in the radial direction can be compensated by the further first bellows portion and the further second bellows portion coming into closer proximity to one another, whereby the mechanical stresses in the central region of the first mold piece can be reduced or avoided.

As an alternative or in addition to providing the further bellows, the first mold half may be made thicker than the second mold half. This can achieve the effect that the mechanical stresses occur to a lesser extent in the first mold half than in the second mold half.

The production device preferably comprises a heating device being designed to heat the first mold half and/or the second mold half. It is thereby possible to choose a heat curable liquid for the curable liquid.

The production device preferably comprises an illumination source being designed to illuminate the mold space with electromagnetic radiation. It is thereby possible to choose a liquid that can be cured by electromagnetic radiation for the curable liquid. The illumination source can for example be designed to emit the electromagnetic radiation in a wavelength region from 250 nm to 800 nm, in particular from 380 nm to 650 nm. The illumination source can for example comprise a light emitting diode and/or a lamp, in particular a gas discharge lamp.

The first mold half and/or the second mold half are preferably transparent or semi-transparent for the electromagnetic radiation. This means for example that the first mold half and/or the second mold half respectively have a transmission of at least 50%, in particular at least 70%, when illuminated with the electromagnetic radiation parallel to the optical axis.

The first mold half and/or the second mold half are preferably transparent in a wavelength region from 250 nm to 800 nm, in particular from 380 nm to 650 nm. This means for example that the first mold half and/or the second mold half respectively have a transmission of at least 50%, in particular at least 70%, when illuminated with the electromagnetic radiation parallel to the optical axis.

The first mold half and/or the second mold half preferably comprise plastic or preferably consist of the plastic. The plastic preferably comprises at least one substance that is chose from the group: Cyclic olefine copolymer (COC), polyethylene (PE), polypropylene (PP). The cyclic olefine copolymer is commercially available, for example, under the name Topas. The plastic is preferably chemically inert. The plastic preferably has a modulus of elasticity in compression in a region of 0,1 GPa to 1, 6 GPa, in particular of 0,8 GPa to 1,6 GPa, and a modulus of elasticity in tension in a region of 0,1 GPa to 1, 6 GPa, in particular of 0,8 GPa to 1,6 GPa.

The central region of the first mold half and/or the central region of the second mold half preferably have a roughness $S_a$ in a range from 1 nm to 50 nm, in particular in a range from 1 nm to 20 nm. The haptic area of the first mold half and/or the haptic area of the second mold half preferably have, in order to produce a smooth haptic, a roughness $S_a$ in a range from 1 nm to 100 nm, in particular in a range from 1 nm to 40 nm. The haptic region of the first mold half and/or the haptic region of the second mold half preferably have, in order to produce a rough haptic, a roughness $S_a$ in a range from 100 nm to 2.0 µm. The rough haptic has the advantage that it can be fixed more firmly in the capsular bag than the smooth haptic. The roughness $S_a$ is defined as the mean arithmetic height according to ISO 25178. The roughness $S_a$ can be measured, for example, with a white light interferometer.

Preferably, the first mold half and/or the second mold half respectively is a single-use component.

The production device can have an assembly tool that is designed to insert the second mold half into the outer ring in the inserting direction. The assembly tool can, for example, be designed to insert the second mold half in a position-controlled manner. Alternatively, the assembly tool can be designed, for example, to insert the second mold half in a force-controlled manner. The assembly tool can be designed to stop inserting the second mold half when a maximum force is exceeded. This can prevent bending of the first mold half and/or the second mold half. In addition, the assembly tool can be designed to remove the second mold half from the outer ring. Furthermore, the assembly tool may be designed to grip the reinforcing projection.

For example, the fluid may comprise a mixture comprising an acrylate monomer, a methacrylate monomer, and a crosslinker. The crosslinker can for example be selected from the group: BDDA (1,4-butanediol diacrylate), EGDMA (ethyleneglycole dimethacrylate), TMPTA (Trimethylolpropane triacrylate). For example, such a mixture is commercially available under the trade name Acrylmex as a finished intraocular lens. The liquid may also have a photoinitiator. This allows the liquid to be cured by irradiation with the electromagnetic radiation. For this purpose, the wavelength of the electromagnetic radiation may be selected such that the electromagnetic radiation occurs in an absorption band of the photoinitiator. Preferably, the photoinitiator comprises at least one substance selected from the group: 2,2-dimethoxy-1,2-diphenylethane-1-one (Irgacure 651), bis (2,4,6-trimethylbenzoyl)phenylphosphine oxide (Irgacure 819), diphenyl(2,4,6-trimethylbenzoyl)phosphine oxide (Irgacure TPO), camphorquinone, 4-dimethylamino-benzoic acid ethyl ester.

The process according to the invention for producing an intraocular lens blank comprises the steps of: a) providing the production device according to the invention or an embodiment thereof; b) arranging the first mold half and the second mold half in the spacing state; c) applying the liquid to the first mold half and/or the second mold half; d) inserting the second mold half in the inserting direction into the outer ring, whereby the first mold half and the second mold half are brought into the proximity state and the liquid is arranged in the molding space; e) curing the liquid.

In step a), the first mold half and/or the second mold half are preferably produced in each case by a molding process, in particular injection molding. It is conceivable that step a) additionally comprises polishing, in particular laser polishing, and/or turning of the first mold half and/or the second mold half. In this way, for example, a desired roughness can be set. It is also conceivable that during polishing and/or turning the first tool half and/or the second tool half are cooled, in particular to a temperature in a region from −20° C. to 0° C.

It is preferred that, in step e), an intraocular lens blank is formed and the process comprises the steps of: f) removing the first mold half and/or the second mold half from the intraocular lens blank; g) completing an intraocular lens by machining the intraocular lens blank, in particular by a removal of material, for example milling, turning and/or laser removal. In particular, the haptic element may be produced by the machining. It is particularly preferred that, in step g), one of the two mold halves remains on the intraocular lens blank. As a result, the intraocular lens blank has a greater strength in step g). Moreover, by turning one of the two mold halves, the orientation of the intraocular lens blank can be set particularly easily.

In step e), the curing preferably takes place by heating of the liquid and/or by applying electromagnetic radiation, in particular in a wavelength region from 250 nm to 800 nm or from 380 nm to 650 nm, to the liquid. The duration of the illumination can, for example, range from 1 minute to 180 minutes. Short durations are more suitable if the liquid contains prepolymers, longer durations are more suitable if the liquid contains monomers. For example, the intensity with which the first mold half and/or the second mold half are illuminated can each be in a range from 2 mW/cm$^2$ to 25 mW/cm$^2$.

It is conceivable that the fluid is tempered, in particular heated, for example to a temperature of 10° C. to 50° C., before the fluid is illuminated with the electromagnetic radiation.

It is conceivable that in step a) a plurality of the first mold halves and a plurality of the second mold halves are provided, steps b) to d) are carried out for all the first mold halves and all the second mold halves, and in step e) the liquid is cured in all the molding spaces simultaneously. For example, in step a), it is conceivable to arrange the plurality of the first mold halves or the plurality of the second mold halves on a common tray.

The intraocular lens blank according to the invention comprises an optical body having an optical axis, a haptic region attached to the optical body, arranged outside the optical body in a radial direction with respect to the optical axis and extending fully circumferentially around the optical body in a circumferential direction with respect to the optical axis, and from which a haptic of the intraocular lens can be formed by mechanically processing the haptic region, and an intraocular lens bellows disposed outside the haptic region in the radial direction and attached to the haptic region. By providing the intraocular lens bellows, the intraocular lens blank advantageously has a high strength against bending. This is particularly relevant when the intraocular lens blank is removed from the production device or is subjected to following process steps, for example an extraction in the solvent or a drying. The intraocular lens blank may, for example, be manufactured by a casting process.

It is preferred that the intraocular lens blank is manufactured by means of the production device and/or the method.

Mechanical processing of the haptic region may include removal of material, such as milling.

The intraocular lens blank according to the invention is produced by means of the production device according to the invention or a preferred embodiment thereof and/or by means of the method according to the invention or a preferred embodiment thereof.

Figure 2:
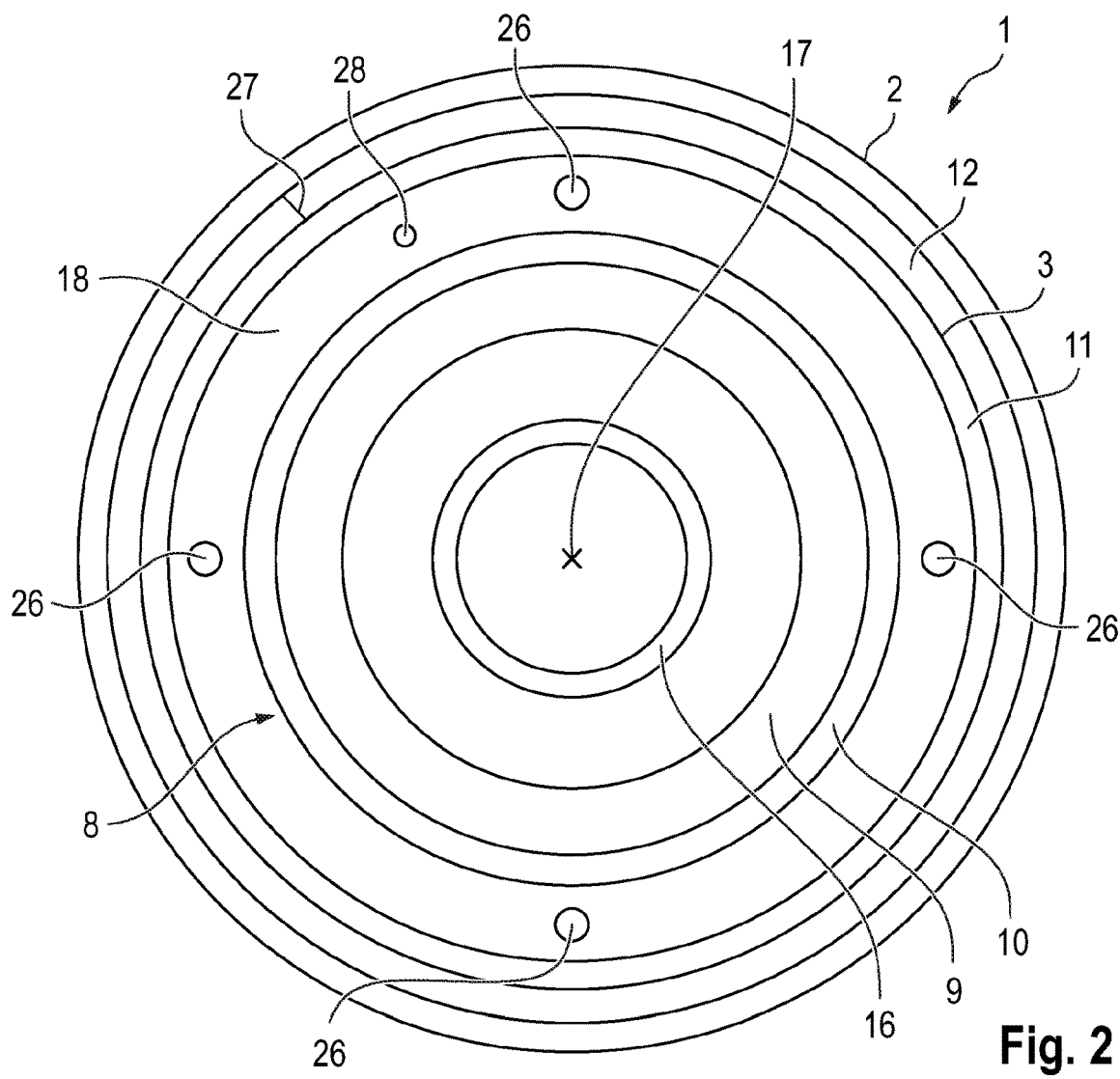
Figure 3:
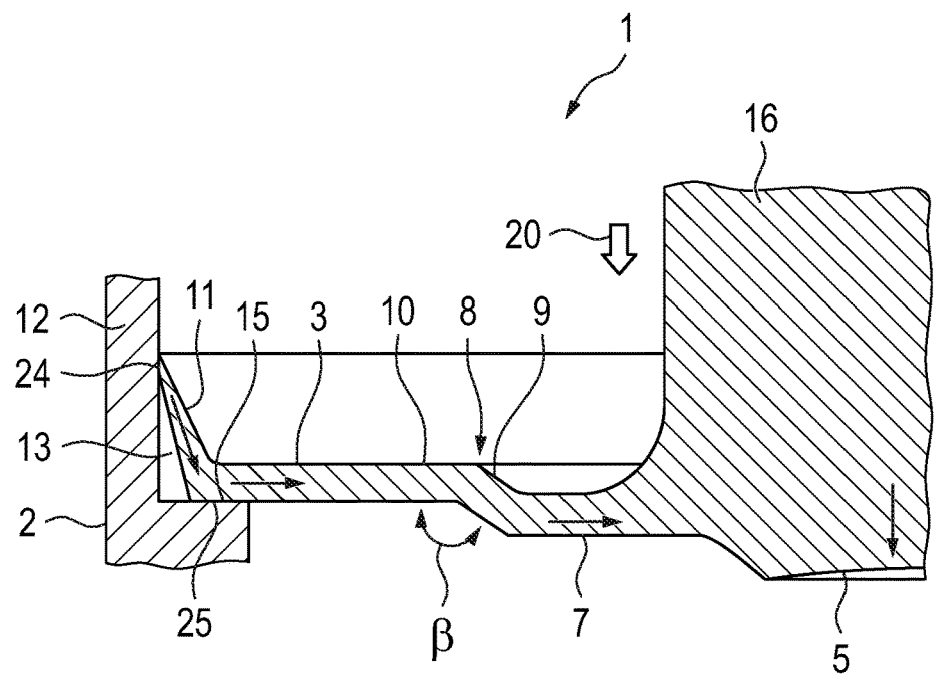
Figure 4:
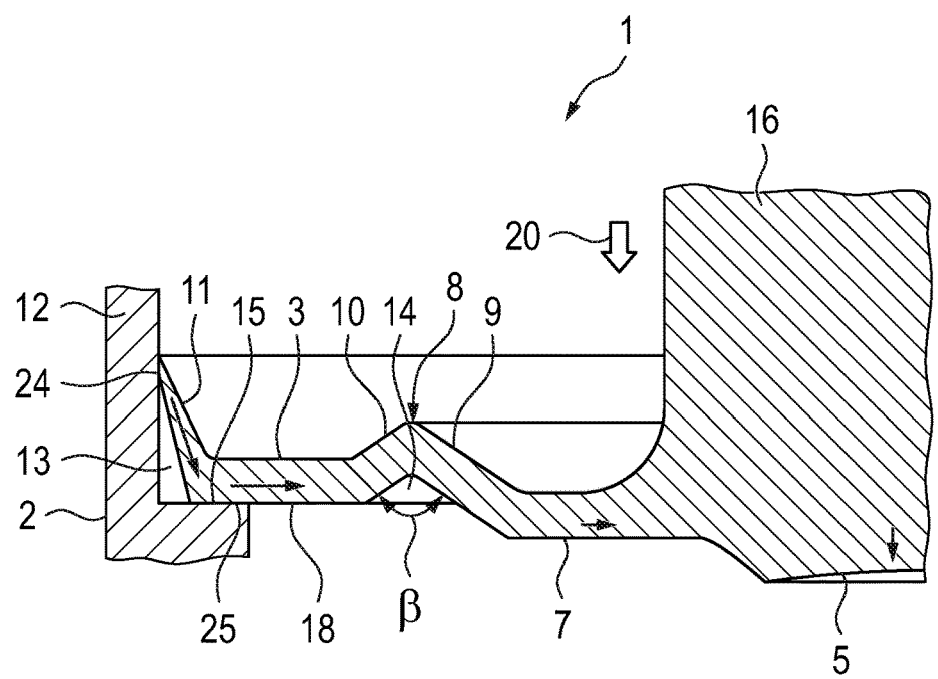
Figure 5:
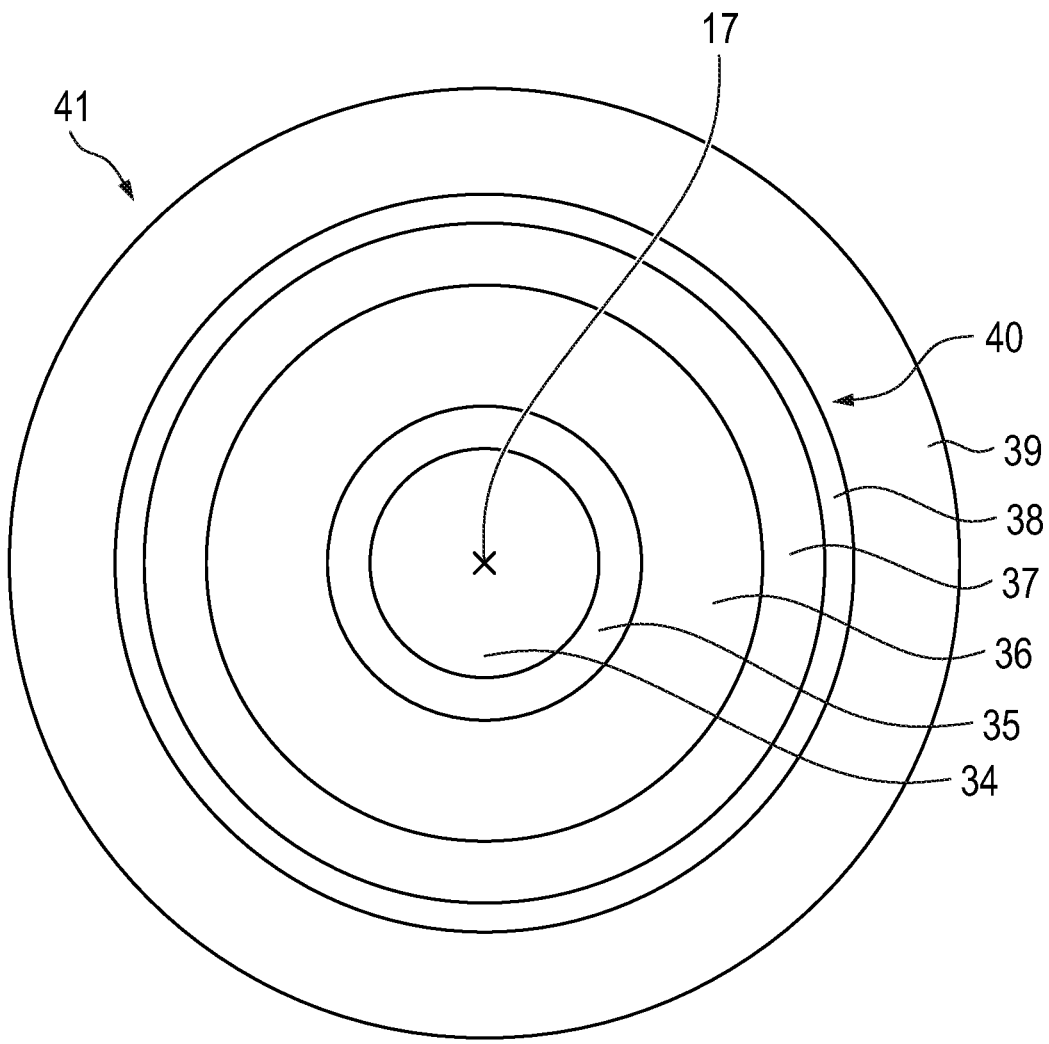

The invention is explained in more detail below with reference to the appended schematic drawings, in which:

FIG. 1 shows a longitudinal section through a first embodiment of the production device, FIG. 2 shows a plan view from above of the first embodiment, FIG. 3 shows a longitudinal section through a second embodiment of the production device and FIG. 4 shows a longitudinal section through a third embodiment of the production device and FIG. 5 shows a top view of an intraocular lens blank.

As can be seen from FIGS. 1 to 4, a production device 1 for producing an intraocular lens blank 41 has a first mold half 2, which has an outer ring 12, and a second mold half 3. The first mold half 2 and the second mold half 3 have a spacing state, in which the second mold half 3 is arranged outside the outer ring 12, and a proximity state, in which the second mold half 3 is clamped in the outer ring 12 as a result of inserting the second mold half 3 in an inserting direction 20, and the first mold half 2 and the second mold half 3 delimit a molding space 19 in which a curable liquid is intended to be arranged for producing the intraocular lens blank 41. The first mold half 2 has a central region 4 of the first mold half 2 and the second mold half 3 has a central region 5 of the second mold half 3, the central region 4 of the first mold half 2 and the central region 5 of the second mold half 3 respectively having the form of one of the two end faces of an optical body of the intraocular lens blank 41. The end faces are those faces of the optical body at which light passing through the lens is refracted in order to carry out optical imaging. For this purpose, at least one of the two end faces may be curved. The second mold half 3 has a bellows 8, which extends fully circumferentially around the central region 5 of the second mold half 3 in a circumferential direction 23 with respect to an optical axis 17 of the optical body. The bellows 8 has a first bellows portion 9 and a second bellows portion 10, which is arranged directly outside the first bellows portion 9 in a radial direction 22 with respect to the optical axis 17 and, in the spacing state, forms with the first bellows portion 9 a first angle α (the spacing state is not shown in the figures, and consequently the angle α is not shown), which is smaller than 180°, and, in the proximity state, forms with the first bellows portion 9 a second angle β, which is smaller than the first angle, i.e. α>β. The inserting direction 20 may be arranged parallel to an axial direction 21 with respect to the optical axis 17, compare FIGS. 1, 3 and 4.

In FIGS. 1, 3 and 4, it is shown that the inserting direction 20 is oriented downward, though other orientations for the inserting direction 20 are also conceivable.

FIG. 2 shows that, in the proximity state, the second mold half 3 can contact the outer ring 12 fully circumferentially in the circumferential direction 23, whereby a first seal 24 (compare FIGS. 1, 3 and 4) is formed by the outer ring 12 and the second mold half 3, fully circumferentially in the circumferential direction 23. This means in other words that contact between the second mold half 3 and the outer ring 12 can be formed in the circumferential direction 23 without interruptions. FIG. 2 also reveals that the bellows 8 may for example be formed as circular. FIG. 2 similarly reveals that the first bellows portion 9 and the second bellows portion 10 may be formed rotationally symmetrically with respect to the optical axis 17.

As can be seen from FIGS. 1, 3 and 4, the first mold half 2 may have a stop 15, which extends fully circumferentially in the circumferential direction 23, the second mold half 3 being designed to come up against the stop 15 at the end of the insertion, whereby, in the proximity state, a second seal 25 is formed by the stop 15 and the second mold half 3, fully circumferentially in the circumferential direction 23. This means in other words that the second seal 25 can be formed in the circumferential direction 23 without interruptions.

The second mold half may have a lip 11, which is that part of the second mold half 3 that contacts the outer ring 12 and projects from the rest of the second mold half 3 counter to the inserting direction 20 and outward in the radial direction 23, whereby, in the proximity state, an outer cavity 13 is delimited by the lip 11 and the outer ring 12. The outer cavity 13 may be delimited in the radial direction 22 by the lip 11 and the outer ring 12 and be delimited in the axial direction 21 by that part of the first mold half 2 that is arranged directly adjacent to the outer ring 12 and by the lip 11. Moreover, the outer cavity 13 may be sealed off by the first seal 24 and the second seal 25. FIG. 1 shows that the second mold half 3 may have a connecting portion 18, which is fastened to the bellows 8, in particular to the second bellows portion 10, and to the lip 11 and connects the bellows 8, in particular the second bellows portion 10, to the lip 11. In the proximity state, the connecting portion 18 may contact the stop 15.

As can be seen from FIGS. 1, 3 and 4, in the proximity state, the first bellows portion 9 may form the inner end of the bellows 8 in the radial direction 22, and may thus be inclined in relation to the optical axis 17 such that a distance of the first bellows portion 9 from the optical axis 17 becomes shorter in the inserting direction 20, the central region 5 of the second mold half 3 being fastened to the inner end of the first bellows portion 9 in the radial direction 22. In FIGS. 3 and 4, the arrows indicate a flow of force resulting from the insertion of the second mold part 3 into the outer ring 12. Via the lip 11, a force enters the bellows 9 inwardly in the radial direction 22, whereby the first bellows portion 9 and the second bellows portion 10 come into closer proximity to one another. As a result, as the second mold part 2 is inserted into the outer ring 12, the outer end of the first bellows portion 9 in the radial direction 22 is displaced counter to the inserting direction 20 and the inner end of the first bellows portion 10 in the radial direction 22 is displaced in the inserting direction 20. Because the central region 5 of the second mold half 3 is fastened to the inner end of the first bellows portion 9 in the radial direction 22, the central region 5 of the second mold half 3 is also displaced in the inserting direction 20. As a result, shrinking of the liquid during its curing can be compensated.

FIG. 1 shows that the first mold half 2 may have a further bellows 31, which extends fully circumferentially around the central region 4 of the first mold half 2 in a circumferential direction 23 with respect to the optical axis 17 and has a further first bellows portion 32 and a further second bellows portion 33, which is arranged directly outside the further first bellows portion 32 in a radial direction 22 with respect to the optical axis 17 and, in the spacing state, forms with the further first bellows portion 32 a further first angle, which is smaller than 180°, and, in the proximity state, forms with the further first bellows portion 32 a further second angle, which is smaller than the further first angle. It is also conceivable that, in the proximity state, the further first bellows portion 31 forms the inner end of the further bellows 31 in the radial direction 22, and is thus inclined in relation to the optical axis 17 such that a distance of the further first bellows portion 32 from the optical axis 17 becomes shorter in the inserting direction 20, the central region 4 of the first mold half 2 being fastened to the inner end of the further first bellows portion 31 in the radial direction 22. This achieves the effect that, when deforming of the further bellows 31 occurs in the proximity state, caused by the further first bellows portion 32 coming into closer proximity to the further second bellows portion 33, a displacement of the central region 4 of the first mold half 2 toward the second mold half 3 may take place in the axial direction 21, whereby shrinking of the liquid due to its curing can be advantageously compensated. The further second bellows portion 33 may for example either be oriented in the radial direction 22 (not shown in FIG. 1) or be inclined in relation to the optical axis 17 such that a distance of the second bellows portion 10 from the optical axis 17 becomes longer in the inserting direction 20 (see FIG. 1).

In the case of the first embodiment according to FIGS. 1 and 2 and the third embodiment according to FIG. 4, the second bellows portion 10 is inclined in relation to the optical axis 17 such that a distance of the second bellows portion 10 from the optical axis 17 becomes longer in the inserting direction 20. In the case of the second embodiment according to FIG. 2, by contrast, in the proximity state the second bellows portion 10 is oriented in the radial direction 22. The displacement of the central region 5 of the second mold half 3 in the inserting direction 20 is longer for the second embodiment than for the first and third embodiments, as indicated by the vertical arrows of different lengths in FIGS. 3 and 4.

As can be seen from FIG. 1, the first mold half 2 may delimit an inner cavity 14, which is part of the molding space 19, is arranged outside the central region 5 of the second mold half 3 in the radial direction 22 and, in the case where the inserting direction 20 is oriented downward, is arranged above a region of the molding space 19, it being intended for the optical body to be formed in the region. For example, the inner cavity 14 may be delimited by the bellows 8, in particular by the first bellows portion 9 and the second bellows portion 10.

FIG. 1 shows that the second mold half 3 may have a haptic region 7 of the second mold half 3, which is arranged in a radial region in which a haptic element is intended to be formed from the cured liquid in order to form an intraocular lens from the intraocular lens blank 41 and which is arranged inside the bellows 8 in the radial direction 22. By analogy with this, the first mold half 2 may have a haptic region 6 of the first mold half 2, which is arranged in the radial region in which the haptic region 7 of the second mold half 3 is also arranged.

As can be seen from FIGS. 1 to 4, the second mold half 3 may have a reinforcing projection 16, which projects counter to the inserting direction 20 from regions of the second mold half 3 adjacent to the reinforcing projection 16 and is arranged inside the bellows 8 in the radial direction 22. The reinforcing projection 16 may for example be formed rotationally symmetrically, compare FIG. 2. FIG. 1 shows that the reinforcing projection 16 may be annular and, in the proximity state, arranged concentrically around the optical axis 17. In FIG. 1, it is shown that, in a cross section in which the optical axis 17 is completely arranged, the reinforcing projection 16 may have for example two rectangular forms. It is alternatively conceivable that, in the cross section in which the optical axis 17 is completely arranged, the reinforcing projection 16 has two forms, in which the reinforcing projection 16 in each case becomes narrower with increasing distance from the molding space 19. As a result, in the case where the second mold half 3 is produced by a molding process, in particular injection molding, the second mold half 3 can be easily demolded. FIGS. 3 and 4 show that the reinforcing projection 16 may be cylindrical and, in the proximity state, may be arranged concentrically in relation to the optical axis 17. In FIGS. 3 and 4 it is shown that, in a cross section in which the optical axis 17 is completely arranged, the reinforcing projection 16 may have for example one rectangular form. It is alternatively conceivable that, in the cross section in which the optical axis 17 is completely arranged, the reinforcing projection has a form in which the reinforcing projection 16 becomes narrower with increasing distance from the molding space 19. As a result, in the case where the second mold half 3 is produced by a molding process, in particular injection molding, the second mold half 3 can be easily demolded.

FIGS. 1 and 2 show that the second mold half 2 may have one or more through-holes 26, via which the liquid can leave the molding space 19. As a result, excess liquid can flow away. The through-hole 26 or the through-holes 26 may for example be arranged in the connecting portion 18. As an alternative or in addition, it is conceivable that the through-hole 26 or the through-holes 26 is/are arranged in the first mold half 2.

The first mold half 2 may have a first marking 27, which is designed to mark a circumferential position of the first mold half 2, and the second mold half 3 may have a second marking 28, which is designed to mark a circumferential position of the second mold half, compare FIG. 2. As a result, a relative orientation of the first mold half 2 in relation to the second mold half 3 can be set, for example in that, in the proximity state, the second mold half 3 and/or the first mold half 2 is/are turned about the optical axis 17 until the first marking 27 and the second marking 28 are oriented in the same radial direction 22, it being shown in FIG. 2 that the first marking 27 and the second marking 28 are not oriented in the same radial direction 22. The first marking 27 and/or the second marking 28 may have the form of a projection, so that the first marking 27 and/or the second marking 28 can be taken hold of in order to turn the first mold half 2 and/or the second mold half 3 in relation to one another about the optical axis 17. As an alternative, it is conceivable that the first marking 27 and/or the second marking 28 is/are formed by a line and/or a notch. The notch has the advantage over the projection that, as a result, the mechanical properties, in particular the mechanical stress, during the shrinking of the liquid is/are more homogeneous.

As can be seen in FIG. 5, an intraocular lens blank 41 has an optical body 34, a haptic region 36, and an intraocular lens bellows 40. The optical body 34 has an optical axis 17. The haptic region 36 is fastened to the optical body 34, is arranged outside the optical body 34 in a radial direction 22 with respect to the optical axis 17, and extends fully circumferentially around the optical body 34 in a circumferential direction 23 with respect to the optical axis 17. A haptic of the intraocular lens can be formed from the haptic region 36 by mechanically processing the haptic region 36. The intraocular lens bellows 40 is arranged outside the haptic region 36 in the radial direction 22 and is fastened to the haptic region 36. The intraocular lens blank 41 may be formed by a casting process. Mechanical processing of the haptic region 36 may include, for example, removal of material, such as milling.

FIG. 5 shows that the intraocular lens blank 41 may have a transition region 35 extending fully circumferentially 23 around the optical body 34, and the haptic region 36 may be indirectly fastened to the optic body 34 via the transition region 35. It is conceivable that the haptics are not formed from the transition region 35. Alternatively, it is conceivable that the transition region 35 is not provided and the haptic region 36 is attached directly to the optical body 34. In addition, FIG. 5 shows that the intraocular lens blank 41 may have an annular region 39 which is arranged outside the intraocular lens bellows 40 in the radial direction 22 and which extends fully circumferentially 23 around the intraocular lens bellows 40. The intraocular lens bellows 40 may include a first intraocular lens bellows portion 37 and a second intraocular lens bellows portion 38 attached immediately outside the first intraocular lens bellows portion 37 in the radial direction 22. The first intraocular lens bellows portion 37 and the second intraocular lens bellows portion 38 enclose an angle that is less than 180°.

In the example shown in FIG. 5, the intraocular lens blank 41 was produced using the production device 1 of FIG. 1 with the difference that no through hole 26 is provided. FIG. 5 shows a top view from FIG. 1. The cross-section of the intraocular lens blank 41 according to FIG. 5 corresponds to the shape of the molding space 19 in the radial direction 22 within the first seal 24. However, it is also conceivable in principle that the curable liquid reaches the outer cavity 13. In this case, the intraocular lens blank 41 would have a first further region outside the ring region 39, which has the shape of a further ring caused by the first seal 24, and subsequently have a second further region which originates from liquid cured in the outer cavity 13.

LIST OF REFERENCE SIGNS

1 Production device
2 First mold half
3 Second mold half
4 Central region of the first mold half
5 Central region of the second mold half
6 Haptic region of the first mold half
7 Haptic region of the second mold half
8 Bellows
9 First bellows portion
10 Second bellows portion
11 Lip
12 Outer ring
13 Outer cavity
14 Inner cavity
15 Stop
16 Reinforcing projection
17 Optical axis
18 Connecting portion
19 Molding space
20 Inserting direction
21 Axial direction
22 Radial direction
23 Circumferential direction
24 First seal
25 Second seal
26 Through-hole
27 First marking
28 Second marking
31 Further bellows
32 Further first bellows portion
33 Further second bellows portion
34 Optical body
35 Transition region
36 Haptic region
37 First intraocular lens bellows portion
38 Second intraocular lens bellows portion
39 Ring region
40 Intraocular lens bellows
41 Intraocular lens blank
α First angle
β Second angle

The invention claimed is:

1. A production device for producing an intraocular lens blank, with a first mold half, which has an outer ring, and a second mold half, which have a spacing state, in which the second mold half is arranged outside the outer ring, and a proximity state, in which the second mold half is clamped in the outer ring as a result of inserting the second mold half in an inserting direction, and the first mold half and the second mold half delimit a molding space in which a curable liquid is intended to be arranged for producing the intraocular lens blank, wherein the first mold half has a central region of the first mold half and the second mold half has a central region of the second mold half, the central region of the first mold half and the central region of the second mold half respectively having the form of one of the two end faces of an optical body of the intraocular lens blank, wherein the end faces are those faces of the optical body at which light passing through the lens is refracted in order to carry out optical imaging, and the second mold half has a bellows, which extends fully circumferentially around the central region of the second mold half in a circumferential direction with respect to an optical axis of the optical body and has a first bellows portion and a second bellows portion, which is arranged directly outside the first bellows portion in a radial direction with respect to the optical axis and, in the spacing state, forms with the first bellows portion a first angle ($\alpha$), which is smaller than 180°, and, in the proximity state, forms with the first bellows portion a second angle ($\beta$), which is smaller than the first angle.

2. A production device for producing an intraocular lens blank, with a first mold half, which has an outer ring, and a second mold half, which have a spacing state, in which the second mold half is arranged outside the outer ring, and a proximity state, in which the second mold half is clamped in the outer ring as a result of inserting the second mold half in an inserting direction, and the first mold half and the second mold half delimit a molding space in which a curable liquid is intended to be arranged for producing the intraocular lens blank, wherein the first mold half has a central region of the first mold half and the second mold half has a central region of the second mold half, the central region of the first mold half and the central region of the second mold half respectively having the form of one of the two end faces of an optical body of the intraocular lens blank, wherein the end faces are those faces of the optical body at which light passing through the lens is refracted in order to carry out optical imaging, and the second mold half has a bellows, which extends fully circumferentially around the central region of the first mold half in a circumferential direction with respect to an optical axis of the optical body and has a first bellows portion and a second bellows portion, which is arranged directly outside the first bellows portion in a radial direction with respect to the optical axis and, in the spacing state, forms with the first bellows portion a first angle, which is smaller than 180°, and, in the proximity state, forms with the first bellows portion a second angle ($\beta$), which is larger than the first angle.

3. The production device as claimed in claim 1, wherein, in the proximity state, the second mold half contacts the outer ring fully circumferentially in the circumferential direction, whereby a first seal is formed by the outer ring and the second mold half, fully circumferentially in the circumferential direction.

4. The production device as claimed in claim 3, wherein the first mold half has a stop, which extends fully circumferentially in the circumferential direction, the second mold half being designed to come up against the stop at the end of the insertion, whereby, in the proximity state, a second seal is formed by the stop and the second mold half, fully circumferentially in the circumferential direction.

5. A process for producing an intraocular lens blank with the steps of:
   a) providing a production device as claimed in claim 1;
   b) arranging the first mold half and the second mold half in the spacing state;
   c) applying the liquid to the first mold half and/or the second mold half;
   d) inserting the second mold half in the inserting direction into the outer ring, whereby the first mold half and the second mold half are brought into the proximity state and the liquid is arranged in the molding space; and
   e) curing the liquid.

\* \* \* \* \*